United States Patent [19]
Taheri

[11] Patent Number: 5,571,176
[45] Date of Patent: Nov. 5, 1996

[54] PARTIALLY AUTOGENOUS FOUR CHAMBERED HEART

[76] Inventor: Syde A. Taheri, 268 Dan Troy, Williamsville, N.Y. 14221

[21] Appl. No.: 41,950

[22] Filed: Apr. 2, 1993

[51] Int. Cl.$^6$ .............................. A61M 1/00; A61K 31/70
[52] U.S. Cl. ..................................... 623/3; 600/17; 514/44
[58] Field of Search .................................. 623/3; 600/16, 600/17, 18; 514/44

[56] References Cited

PUBLICATIONS

Hodgson, "The Vector Void In Gene Therapy" Mar. 1995 Biotechnology vol. 13, pp. 222–225.

*Primary Examiner*—Robert A. H. Clarke
*Attorney, Agent, or Firm*—Lieberman & Nowak

[57] ABSTRACT

An autogenous heart having a physiology similar to a native heart is formed from two muscle segments which are wrapped about a mold and divided to form four chambers. To form this heart, two segments of muscle are formed to surround a silastic balloon reinforced mold which permits gross formation of the heart. The silastic balloon is then deflated and withdrawn. The interior of the heart is subdivided; the four chambers are formed; and valves are emplaced in much the manner as in the native heart. A cardiac assist device formed from a single chamber is made in much the same manner. The cardiac assist device has a single exit vessel which is bifurcated so as to allow blood flow into the chamber as the muscle is relaxed and blood flow out of the chamber as the muscle is contracted. A further improvement over current cardiac assist devices is the use of a compression ring to occlude blood flow within the native vessel when the muscle is contracted.

7 Claims, 7 Drawing Sheets

PARTIALLY AUTOGENOUS FOUR CHAMBERED HEART

BACKGROUND OF THE INVENTION

The subject invention relates to autogenous blood pumping devices which replace or assist a heart in pumping blood. Since the material used in the construction of the heart/assist is derived mainly from native tissue, problems with immunorejection are minimized.

There are approximately 250,000 new cases of cardiomyopathy in the United States yearly. Five year survival of these cases is approximately 25%. Because of insufficient number of homologous heart donors, a new heart source is needed. The subject invention provides autogenous heart suitable for this group of patients.

A series of patents to Pierre-Andre Grandjean (U.S. Pat. Nos. 5,069,680, 5,089,019, 5,098,442, issued Dec. 3, 1991, Feb. 18, 1992 and Mar. 24, 1992, respectively, the contents of which are herein incorporated by reference), describe muscle stimulators and apparatuses and methods for their control. The Grandjean patents deal with skeletal muscle use in a cardiac assist system. As described by Grandjean, cardiac muscle can be used in direct circumscription of a human heart to assist the heart in contracting. Alternatively, the heart assist can be an artificial chamber which is inserted in series within the descending aorta or distally connected to a major artery.

U.S. Pat. No. 5,007,927, issued Apr. 16, 1991 to Badylak, et al. teaches a muscle-powered cardiac assist device (the contents of this patent are herein incorporated by reference). This cardiac assist device is formed from rectus abdominis muscle and latissimus dorsi muscle in which the skeletal muscle has been modified to decrease fatigue through the use of electrical stimuli, which promotes conversion of fast twitch muscle fibers into slow twitch muscle fibers. As is known, slow twitch muscle fiber has a greater tolerance for long term contractile loading.

U.S. Pat. No. 4,411,268, issued Oct. 25, 1983 to Cox, teaches a muscle stimulator useful for inducing a functional contraction in muscle tissue while conditioning the contractile properties of that tissue (the contents of this patent are herein incorporated by reference).

The subject invention provides an autogenous four-chamber heart which is meant as an alternative to heart transplants and the mechanized replacement hearts currently used when the native heart is unable to function and provides the following advantages: Immunoreaction and possible rejection are essentially eliminated since the materials employed are autogenous. No heart donor is required, eliminating the tissue matching and waiting process. A "spare heart" can augment a deficient native heart while retaining benefits provided by the native heart.

The subject invention also provides an autogenous cardiac assist device which is meant to supplement a deficient heart and provides the following advantages: Immunoreaction and possible rejection are essentially eliminated. No donor is required. Placement can be proximate or distant to the heart. Multiple assists can be employed in a single patient. A single opening permits greater muscle circumscription of the chamber.

SUMMARY OF THE INVENTION

A method is disclosed for making an autogenous four chambered heart. This comprises providing two segments of autogenous muscle. The first segment provides the force for contracting the upper two chambers and the second segment provides the force for contracting the lower two chambers. The two segments are wrapped about a mold of predetermined size to form a cavity by enclosing the mold within the two muscle segments. The cavity is then segmented into two sections so that each section is surrounded by approximately one-half of the first muscle segment and one-half of the second muscle segment. The two sections are then divided so as to form four chambers, each chamber having an exterior wall defined by a portion of either the first or second muscle segment, but not both. Valves are installed between the upper and lower chambers to permit single direction flow of a fluid from the upper chamber to the lower chamber. Each chamber is then connected to the blood vessel corresponding to that found in a native heart.

The invention also provides a method of forming a cardiac assist device by the formation of a section of muscle around an inflatable balloon and then withdrawal of the balloon to form a void, implanting a lining within the void, attaching a bifurcated tube to the lining, and connecting the bifurcated tube to tube to the blood vessel.

The invention also provides a cardiac assist device. This comprises a muscle formed about a chamber for containing blood, means for stimulating the muscle to contract, and a bifurcated tube having two branches and an end. The end is connected to the chamber. The first branch has a valve therein and is connected to a blood vessel which permits a flow of blood into the chamber. The second branch has a valve therein and is connected to a blood vessel which permits a flow of blood out of the chamber.

DETAILED DESCRIPTION OF THE INVENTION

The invention will be described in terms of its preferred embodiments. These embodiments are set forth to provide a better understanding of the subject invention, but are not to be construed as limiting. Throughout the specification, various figures will be referenced. Numbering is consistent from figure to figure.

Figure 1:
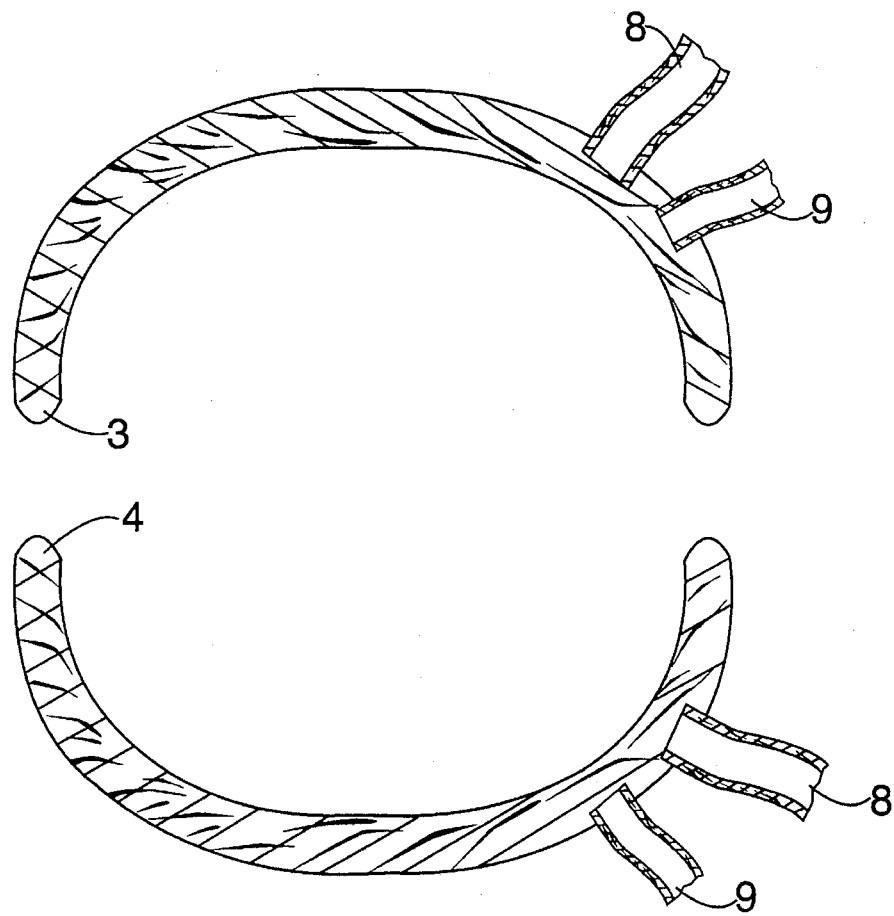
FIG. 1 shows a view of the pectoralis major and latissimus dorsi which are used in construction of the autogenous four chamber heart.

An autogenous four-chamber heart I may be constructed by utilizing two autogenous striated muscles 3 and 4 (or two segments of the same muscle) (see FIG. 1), or from a free muscle patch reinforced by greater omentum 5. One suitable method for bringing greater omentum 5 into the pleural cavity and obtaining muscle patches is described in co-pending patent application Ser. No. 07/857,172 now U.S. Pat. No. 5,327,913, issued Jul. 12, 1994, the contents of which is herein incorporated by reference.

Figure 4:
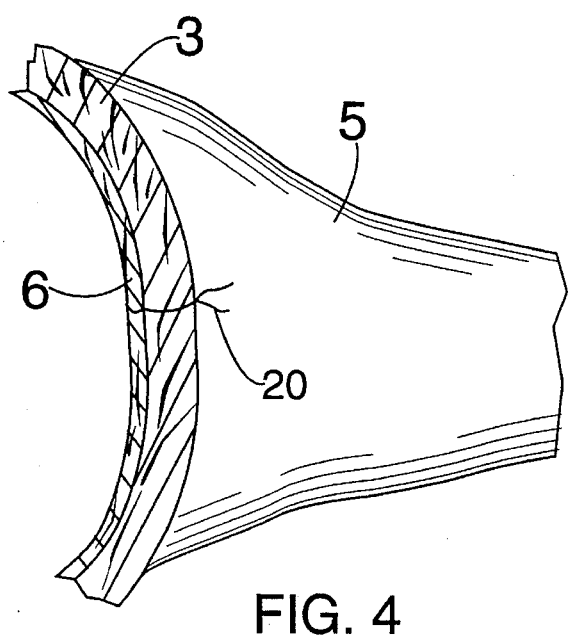
FIG. 4 shows a detailed view of the muscle porcine pericardium and greater omentum interaction.
Figure 2:
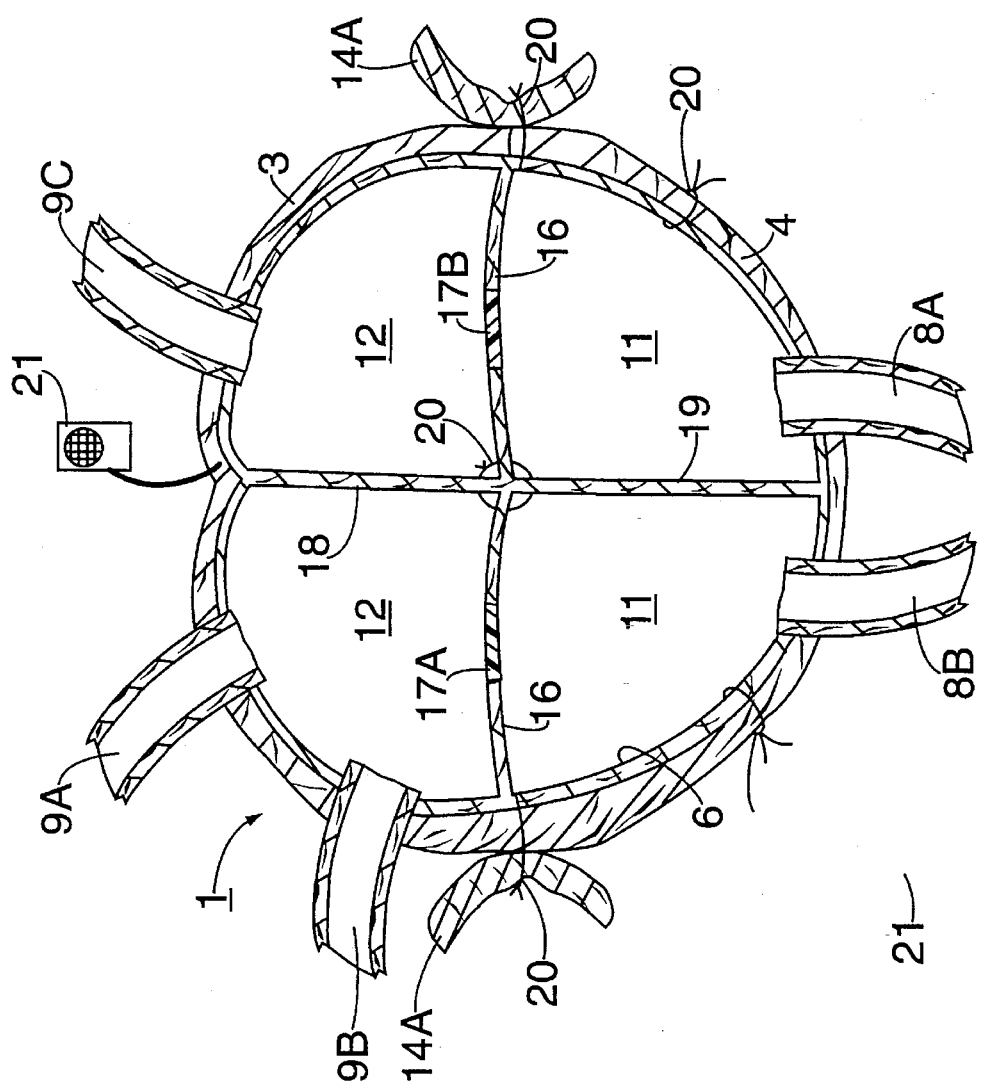
FIG. 2 shows a schematic view of the four chamber heart showing the interrelation between the various blood vessels, latissimus dorsi, pectoralis major and fascia lata.
Figure 3:
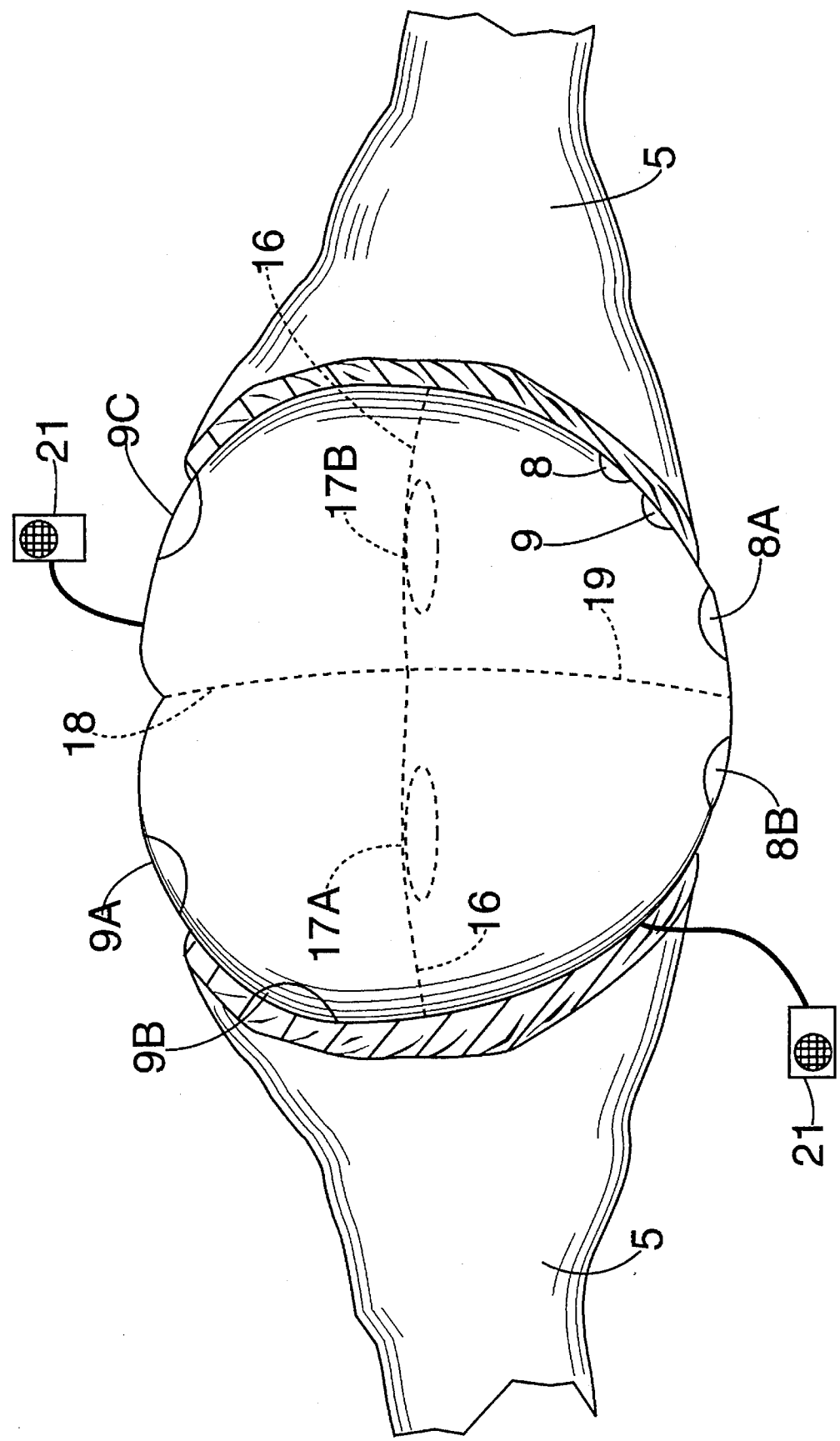
FIG. 3 is another schematic view illustrating the relationship of the four chamber autogenous heart to the greater omentum and the connection points for a pacing device.
Figure 7:
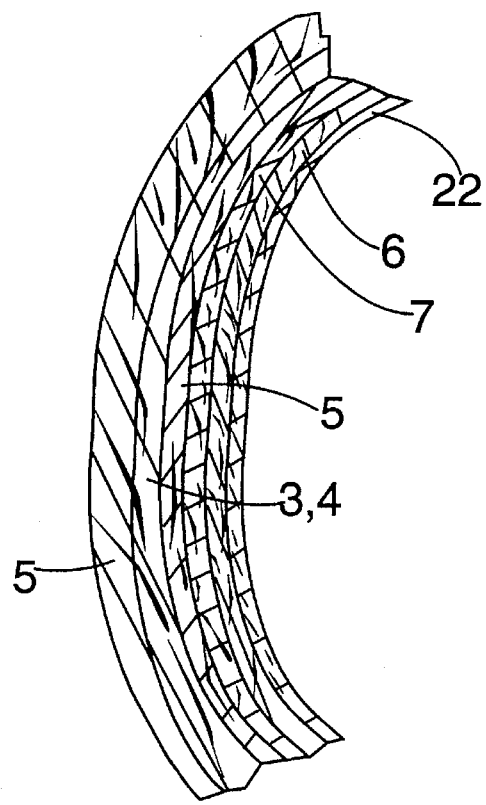
FIG. 7 shows the cross-section of the striated heart shows endothelium, porcine pericardium, mold, greater omentum, striated muscle and greater omentum.

FIGS. 2 and 3 show the general construction of the subject heart. Lining 6 of heart 1 is formed from porcine or bovine pericardium. Chambers are generally constructed over four pre-designed atrial and ventricular molds 7 (typically absorbable). Mold 7 may be either internal or external and serves to shape and size the heart to be constructed. The blood supply for new heart I is derived either from greater omental artery (arteries are generally labeled 8 and veins are generally labelled 9) or native artery and veins of the designated muscle. The inner layer of the heart 6 is generally made from autogenous pleura peritoneum, or porcine or bovine pericardium (see FIG. 4 which also shows the placement of greater omentum 5). This layer may then be covered by a layer of endothelium 22 (see FIG. 7 which shows a cross-section of the layering). As known in the art, the various non-human components described throughout the application can be made non-immunogenic. Most, if not all, of the non-human components presently treated so as to be nonimmunogenic are now commercially available.

The concept behind the autogenous four chamber heart is to utilize a patient's own striated muscles which are physically proximate to each other to construct a heart for transplant into the chest or other location (heterotopic heart). Examples of suitable muscles for striated muscles 3 and 4 are pectoralis 3 and latissimus dorsi 4 or quadriceps 3 and sartorius 4 muscle, e.g. ventricular chambers 11 may be reconstructed from latissimus dorsi 4 and atriums 12 from pectoralis major 3.

Muscles released from their insertions, such as pectoris muscle from the costo-chondral junction of the first rib to six rib as well as tendinous portion of the clavicle, may be used to form heart 1. Nerve 10 and blood supply 8 and 9 for the muscle are typically maintained intact.

Construction of atrium 12 and ventricle 11 is accomplished by wrapping autogenous striated muscle over pre-determined size balloon 13 and/or mold 7 to obtain a desired size ventricular cavity for that individual patient. Balloon 13 is inflatable to act as a mold and deflatable to facilitate removal, if necessary. Additionally, balloon 13 may be rapidly (about 40–50 times per minute) inflated and deflated to facilitate conversion of striated muscle to heart-type muscle (see below). If mold 7 is used, it is usually absorbable by the recipient.

Cavity volume is determined based on the patient's native heart size and/or physiological norms. The outer side of ventricle 11 and atrium 12 may be formed from the fascia 14 of the muscle. The inner sides of atrium 12 and ventricle 11 are typically covered by bovine or porcine pericardium 6. Atrial-ventricular septum 16 may be made from either homologous or heterologous pericardium. The connection between atrium 12 and ventricle 11 typically includes a prosthetic valve 17A or 17B. Outflow from the ventricles (8A or 8B) may include a prosthetic ring incorporated with prostheses to minimize the chance of expansion or collapse of the vessel. Ventricular outflow typically flows through a tubular graft containing a prosthetic valve. Inflow to atrium 12 generally will have two openings, one for superior 9A and another inferior vena cava 9B.

Figure 6:
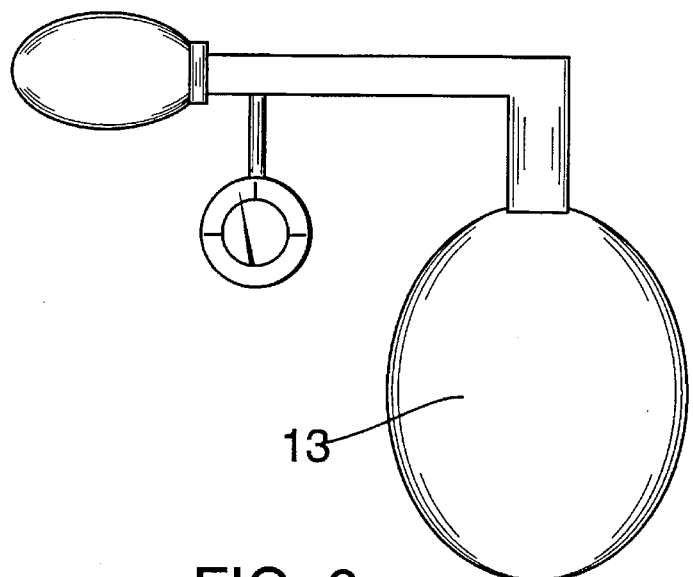
FIG. 6 shows pressure and size control balloon for reconstruction of ventricle.

As stated above, construction of atrium 12 from pectoris major involves mobilizing the muscle from its insertion, while preserving the artery 8, vein 9 and nerve 10. A silastic balloon 13 may then be used to serve as a template for wrapping pectoralis major (see FIG. 6). Normally, atrium 12 has a capacity of 50–60 cm$^3$ of blood. The thickness of the atrium wall is approximately 3–4 mm. Ventricle 11 is made of latissimus dorsi over a mold with normal capacity of about 80–90 cm$^3$ of blood per ventricle. To construct atrial-ventricular septum 16, a predetermined length of bovine pericardium is normally used with two prosthetic valves 17. Valve 17A corresponds to the tricuspid valve and valve 17B corresponds to the mitral valve. Openings of the valve measure approximately 4–6 mm diameter or larger depending on the size of the patient. The atrial septum 18 as well as ventricular septum 19 are made of bovine pericardium which is sewn into ventricle 11 and atrium 12 with sutures 20 (typically non-absorbable).

The blood supply of the heart chambers is provided either by native artery or anastomosis to nearby blood vessel. The two chambers are connected by a nonabsorbable suture 20 and reinforced by autogenous fascia lata 14A (see FIG. 2).

The outflow track of the left atrium is made of opening measuring approximately 8–10 mm for anastomosing to the stump of pulmonary veins 9C. The right ventricular outflow is made of an opening with the ring graft which can be connected to pulmonary artery 8B of the recipient patient. The outflow track of the left ventricle also has covered ring which allows it to be sewn to a prosthetic vascular tubing containing prosthetic valve.

Adapting and converting striated muscle is typically accomplished by stimulating the nerve supply of the muscle over a period of 8–10 weeks (see the Grandjean Patents cited and incorporated hereinabove). A special pacemaker 21 triggered by pressure, volume and/or flow will stimulate atrium 12 and ventricle 11 sequentially for contraction.

The conversion of fatigue fibers to fatigue resistent fibers has been accomplished by as little as approximately six weeks of low frequency stimulus (electrical or mechanical). Atrial ventricular contraction is generally performed by atrium-ventricle (A-V) sequential pacing, mimicking that in nature.

Alternatively, autogenous heart 1 or cardiac assist 22 may have its striated muscle converted to cardiac-type muscle by repeated physical contractions. This may be effected by repeatedly inflating and deflating balloon 13. Inflating and deflating at a rate of about 40–50 times per minute for a period of about 5 to 10 weeks should provide an ample stimulus. For inflating and deflating balloon 13, an inert/ non-toxic gas is generally employed. Such a gas is readily determinable to one skilled in the art and include $N_2$, $CO_2$ and He. Although it is uncertain at present what role cellular modulators (cytokines) have on this process, the proximity of autogenous heart 1 to the native heart should provide any necessary modulators. For cardiac assist devices at distant locations, for example in the leg, the effectiveness of this technique has yet to be evaluated. However, it is possible that physical stimuli alone are enough to effect the metamorphosis of striated to cardiac-type muscle.

Genetic engineering may also be used to convert light chain striated muscle myosin (fast twitch) to heavy chain myocardium myosin (slow twitch). Different pathways may be employed for converting light chain myosin to heavy chain myosin in an autogenous heart 1 or cardiac assist 22.

One method for increasing the ratio of heavy to light chain myosin is by regional delivery of retrovirally mediated foreign genes to the striated muscle cells in need of conversion to heart-type muscle. Essentially, this would be accomplished by taking the known gene which encodes heavy chain myosin and introducing it into a retroviral gene transfer vector, or other suitable vector, and then introducing this gene-vector into the vicinity of the muscle to be transferred. Such a tactic has been shown effective in hepatic cells by Moscioni, et al., In Vivo Regional Delivery of Retrovirally Mediated Foreign Genes to Rat Liver Cells: Need for Partial Hepatectomy for Successful Foreign Gene Expression, Surgery, 113, 3: 304–311 (1993), the contents of which are herein incorporated by reference.

Another method for amplifying heavy chain myosin production is by suppressing light chain myosin production through the use of antisense nucleotides. Antisense nucleotides would be selected to bind with the mRNA which encodes for this protein (light chain myosin). The main advantages with an antisense approach are specificity and point of attack. Antisense targets a unique gene which expression is to be controlled. Thus, only the selected gene's expression is inhibited. This is highly beneficial since normal cell function needs to be maintained. As is rapidly becoming obvious, antisense technology offers fewer adverse side effects.

Since the biotechniques for accomplishing gene transfer are known in the art, they will not be described further. It should be noted however that a four chamber heart or cardiac assist can include free autogenous muscle reinforced by greater omentum 5. These muscles should also be effected by the above techniques.

The following operative technique may be followed for creating an in situ autogenous heart:

1. Anesthetize the patient in the supine position.

2. Identify the pectoris major 3 and latissimus dorsi major 4 muscles. Detach one anchoring end of each muscle and shape the muscles to form atrium 12 and ventricle 11 over an atrial and ventricular absorbable molds 7 while preserving blood and nerve supply to the muscle.

3. Construct the atrial (50–60 cm$^3$) and ventricular (80–90 cm$^3$) cavities.

4. Convert striated muscle to heart-type muscle by continuous inflation/deflation of mold 7 (in this instance a balloon-type mold, such as a silastic balloon 13 is used) at a rate of approximately 40–50 times per minute, or through the use of the genetic techniques described above.

5. After confirming conversion of striated muscle to heart-type muscle by biopsy, emplace the porcine or bovine pericardium 6. The mitral valve, tricuspid valve, aorta and pulmonary arteries are attached as described above. The connection of the aortic outlet is accomplished by prosthetic graft from the aortic outlet to the branches of the aorta such as the subclavian or carotid artery. The venous inlet is connected to the subclavian vein or internal jugular vein.

Moving now to cardiac assist devices, autogenous cardiac assist is a new concept to provide temporary or permanent ventricular contraction from autogenous triative muscle to assist failing heart. The single chamber cardiac assist is a simplified application of the above principles and is constructed over a single ventricular mold. Typically, this ventricular has a lower volume than that of the heart.

Figure 9A:
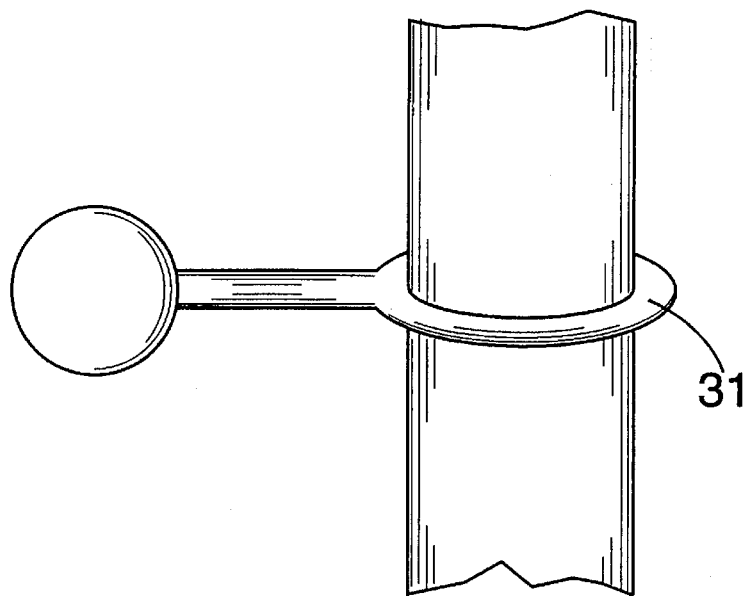
FIG. 9A shows a first depiction of a plastic ring around an artery. During muscle contraction the artery is occluded to improve effectiveness of counter pulsation.
Figure 9B:
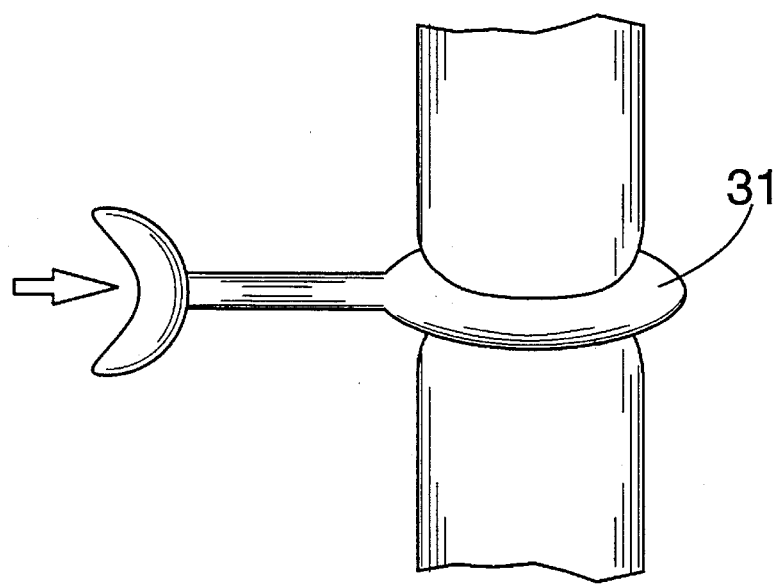
FIG. 9B shows a second depiction of a plastic ring around an artery.

The device employs two autogenous striated muscles (independent muscles or segments of a single muscle), pressure controlled silastic molded balloons 13, bifurcated graft 30 with two prosthetic valves 17 and compression ring 31 to occlude native artery during activation of the assist (see FIGS. 9A and 9B). When the muscles contract, a fluid is forced into compression ring 31 causing it to expand. Since compression ring 31 is substantially identical in diameter to the blood vessel which it surrounds, expansion of compression ring 31 overcomes the outward pressure exerted by the blood vessel, thereby causing the blood vessel to be occluded. Likewise, when the muscle relaxes, compression ring 31 returns to a resting state and allows blood flow through the vessel. Ventricle 11 with inner layer covered by porcine pericardium 6 or the like, is made of trained autogenous striated muscle near or connected with a native arterial system or free patch striated muscle attached to greater omentum 5 which surrounds an absorbable mold 7.

Figure 5:
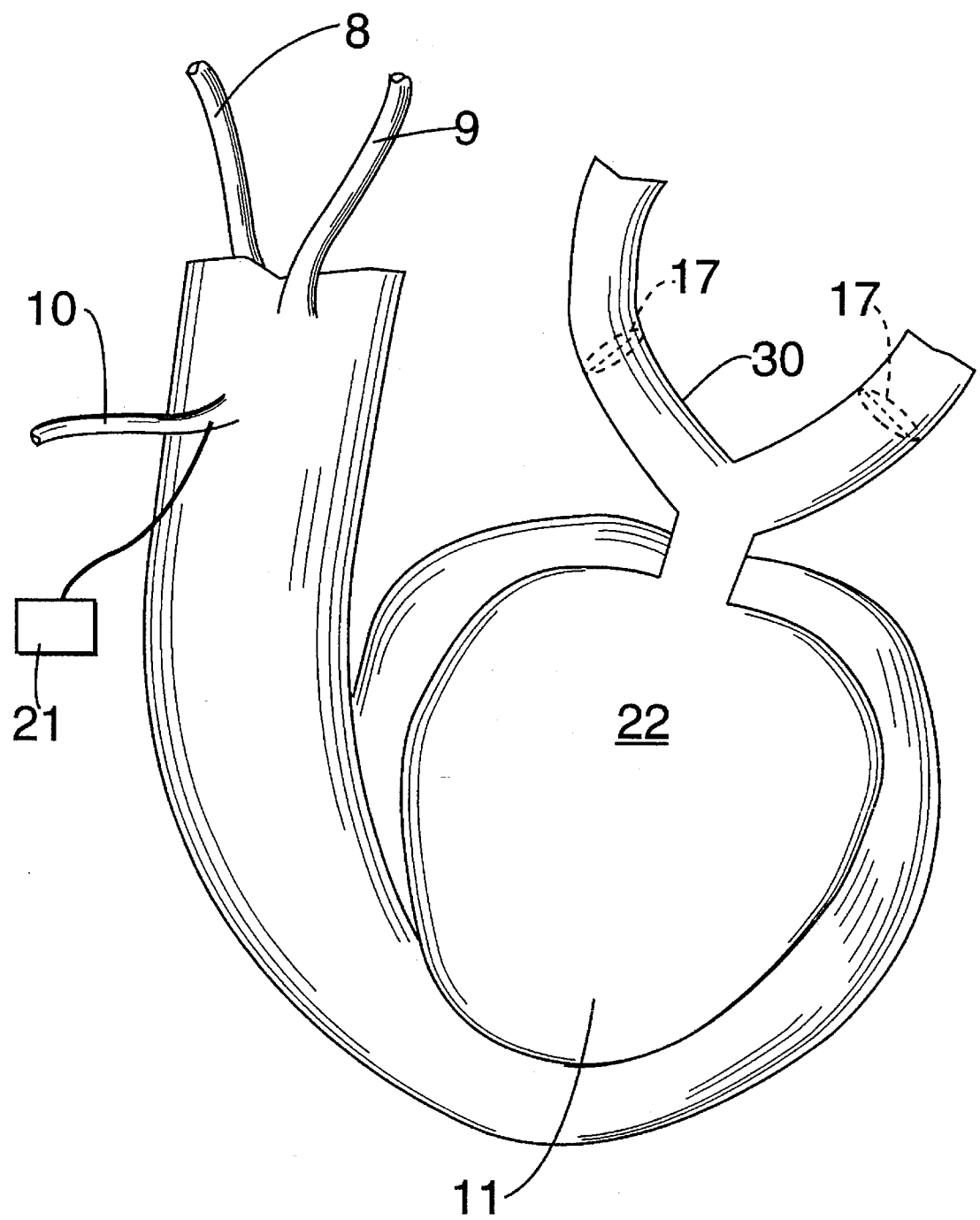
FIG. 5 shows an overview of the subject invention, namely striated muscle ventricle, bifurcated graft with valves and pacemaker stimulating the nerve.
Figure 8A:
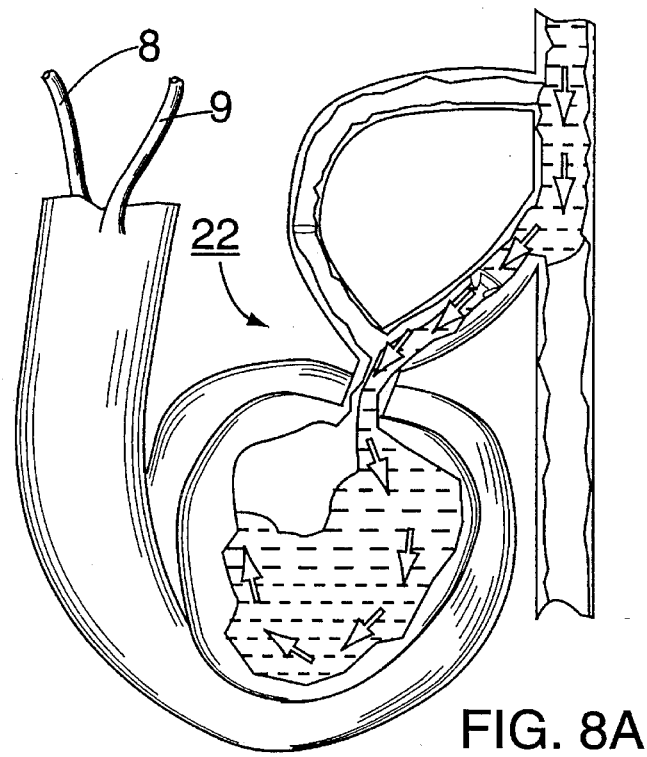
FIG. 8A shows entrance of blood into the cardiac assist device during opening of the prosthetic valve.
Figure 8B:
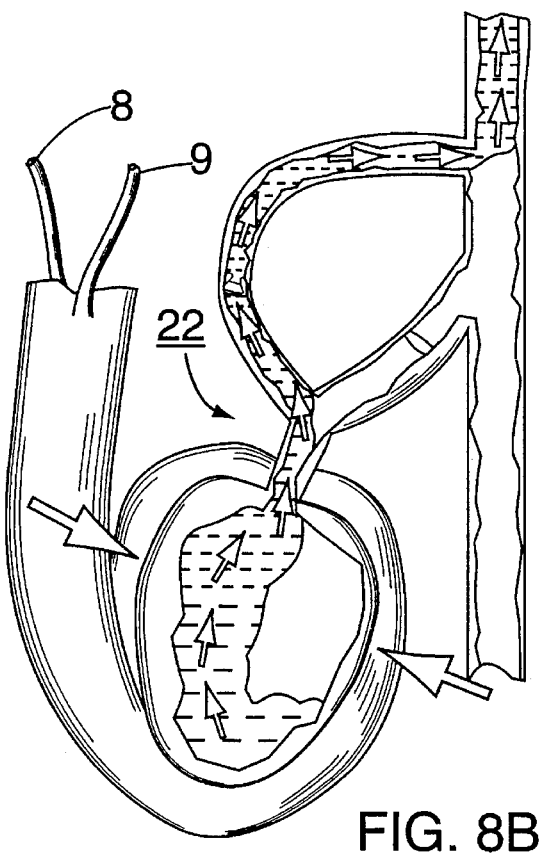
FIG. 8B shows ejection of blood from the cardiac assist device into the aorta.

Vascularization of ventricle 11 is via native blood vessels, or in the case of free autogenous striated muscle, the greater omental artery and vein. The cardiac assist system typically has a capacity of 60 to 80 cm$^3$ of blood during ventricular contraction. The ventricular assist is activated by pacemaker 21 during heart diastole phase. The system is connected to native arterial system of extremities by a bifurcated (Y) graft 30 which contains two prosthetic valves 17 (see FIG. 5). The striated muscle ventricle is filled during systoli and propels blood into arterial system as counter pulsation during diastole (see FIGS. 8A and 8B). This is a new concept with great hope for many patients with severely damaged hearts who need a temporary support or are awaiting heart transplant.

EXPERIMENTAL DETAIL

Free muscle cardiomyoplasty is an alternative to staged latissimus dorsi cardiomyoplasty. Seventeen animals (14 rabbits, 2 dogs and 1 pig) had the left anterior descending artery ligated. Myocardium infarction was confirmed by low blood pressure, ST segment elevation and abnormal CPK with MB band greater than 5%. Fifteen animals had 3 to 5 autogenous free muscle (2 cm×1 cm) cardiomyoplasty reinforced by omental pedicle. Eight weeks post-operation angiography revealed antegrade flow from omentum to myocardium through transplanted muscle. Two animals died without cardio-omentomyoplasty. Transesophegeal echo and Emetron study revealed normal myocardial contraction of myocardial histology eight weeks following surgery, myocardial infarction and marked adhesions of transplanted muscle to myocardium new angiogenesis in regenerated free muscle transplant. Viability of transplanted muscle cell was determined by histology, presence of cytochrome oxidase activity and electrophoretic pattern similar to that of ventricular muscle containing actin and myosin. Histochemical, staining of transplanted muscle showed a prevalence of Type I muscle fibers.

Free muscle transplantation offers an adjunct to staged latissimus dorsi cardiomyoplasty and has potential for supportive therapy in extensive heart disease. Isoenzyme patterns in transplanted skeletal muscle following experimental MI were evaluated. Tissue (100 mg) from normal rectus femoris, left ventricle and transplanted region in porcine and rabbit models at eight weeks post-surgery, were prepared and the supernate analyzed for total CK and LDH expressed in IU/mg wet wt/ml, their isoenzyme profiles in percent, cytochrome oxidase (COX) and cytochrome concentration. Total CK in rectus muscle was 38.4 and 53.3 for pig and rabbit respectively; 15.8 and 16.6 for ventricular tissue and 15.2 and 12.6 in the transplant. Values for total LDH were 4.6 and 4.0 for rectus, 0.9 and 1.0 for ventricle and 0.9 and 0.8 for the transplant. Thus, in both species the change from skeletal to cardiac values were reproducible. Electrophoresis revealed cardiac CK-2 and LDH-5 isoenzyme in the transplant, demonstrating biochemical conversion from the skeletal type profile. Trends in individual cytochrome concentration were observed between skeletal muscle and transplant. Lipid peroxide values in the transplant were similar to those of normal heart and rectus supporting viability of the tissues. These findings suggest that during recovery the enzymatic composition of CK, LDH and COX in skeletal muscle is transformed to one consistent with cardiac muscle.

Upon reading the subject application, various modifications and alternative embodiments will become obvious to those skilled in the art. These variations are to be considered within the scope and spirit of the subject invention, which is only to be limited by the claims which follow and their equivalents.

What is claimed is:

1. A method of forming a four chambered heart, which comprises:

(a) providing two segments of autogenous muscle, the first segment for providing the force for contracting the upper two chambers, the second segment for providing the force for contracting the lower two chambers;

(b) wrapping the two segments about a mold of predetermined size to form a cavity by enclosing the mold within the two muscle segments;

(c) segmenting the cavity into two sections so that each section is surrounded by approximately one-half of the first muscle segment and one-half of the second muscle segment;

(d) dividing the two sections so as to form four chambers, each chamber having an exterior wall defined by a portion of either the first or second muscle segment, but not both;

(e) installing valves between the upper and lower chambers to permit single direction flow of a fluid from the upper chamber to the lower chamber; and (g) connecting each chamber to the blood vessel corresponding to that found in a native heart.

2. A method of claim 1, wherein the two segments of provided muscle comprise pectoralis and latissimus dorsi.

3. A method of claim 1, wherein the two segments of provided muscle comprise free muscle patch reinforced by greater omentum.

4. A method of claim 1 further comprising converting the muscle to cardiac-type muscle by means of a mechanical or electrical stimulus.

5. A method of claim 4, wherein the converting comprises subjecting the muscle to repeated compression and relaxation.

6. A method of claim 5, wherein the compression and relaxation are effected by inflating and deflating a balloon within a cavity, section or chamber.

7. A heart produced by the method of claim 1.

* * * * *